US011730690B2

(12) United States Patent
Anderson

(10) Patent No.: US 11,730,690 B2
(45) Date of Patent: *Aug. 22, 2023

(54) USE OF AMBROXOL TO IMPROVE SKIN BARRIER FUNCTION

(71) Applicant: NeueRe, LLC, Princeton, NJ (US)

(72) Inventor: Stephen Anderson, Princeton, NJ (US)

(73) Assignee: NeueRe, LLC, Princeton, NJ (US)

( * ) Notice: Subject to any disclaimer, the term of this patent is extended or adjusted under 35 U.S.C. 154(b) by 173 days.

This patent is subject to a terminal disclaimer.

(21) Appl. No.: 17/124,798

(22) Filed: Dec. 17, 2020

(65) Prior Publication Data

US 2021/0128438 A1    May 6, 2021

Related U.S. Application Data

(63) Continuation of application No. 16/595,621, filed on Oct. 8, 2019, now Pat. No. 10,894,008, which is a continuation of application No. PCT/US2019/015137, filed on Jan. 25, 2019.

(60) Provisional application No. 62/622,375, filed on Jan. 26, 2018.

(51) Int. Cl.
| | |
|---|---|
| *A61K 8/60* | (2006.01) |
| *A61K 8/44* | (2006.01) |
| *A61Q 5/00* | (2006.01) |
| *A61Q 19/00* | (2006.01) |
| *A61Q 19/08* | (2006.01) |

(52) U.S. Cl.
CPC .............. *A61K 8/60* (2013.01); *A61K 8/44* (2013.01); *A61Q 5/00* (2013.01); *A61Q 19/007* (2013.01); *A61Q 19/08* (2013.01)

(58) Field of Classification Search
CPC ........................................................ A61K 8/60
See application file for complete search history.

(56) References Cited

U.S. PATENT DOCUMENTS

| | | | |
|---|---|---|---|
| 10,894,008 B2 * | 1/2021 | Anderson | A61P 17/02 |
| 2005/0266058 A1 | 12/2005 | Esperester et al. | |
| 2013/0096142 A1 | 4/2013 | Topol et al. | |
| 2014/0161916 A1 | 6/2014 | Khusial et al. | |
| 2018/0296464 A1 | 10/2018 | Graban et al. | |
| 2018/0353397 A1 | 12/2018 | Park et al. | |

FOREIGN PATENT DOCUMENTS

| | | |
|---|---|---|
| CA | 2565183 A1 | 11/2005 |
| JP | 2013099305 A | 5/2013 |
| JP | 2013241398 A | 12/2013 |
| WO | 2006053912 A1 | 5/2006 |
| WO | 2007127439 A3 | 7/2008 |
| WO | 2008021829 A3 | 10/2008 |
| WO | 2009038695 A1 | 3/2009 |
| WO | 2019018247 A1 | 1/2019 |

OTHER PUBLICATIONS

"MIT Technology Review-Old Age is Over! If You Want it", MIT Technology Review, vol. 122, No. 5 The Longevity Issue, (2019).
Abd et al., "Skin Models for the Testing of Transdermal Drugs", Clinical Pharmacology: Advances and Applications, vol. 8, pp. 163-176, (2016).
Agner et al., "Quantification of the DMSO-Response—a Test for Assessment of Sensitive Skin", Clinical and Experimental Dermatology, vol. 14, pp. 214-217, (1989).
Antonov et al., "Methods for the Assessment of Barrier Function ", Curr Probl Dermatol. Basel, vol. 49, pp. 61-70, (2016).
Bank of America Merrill Lynch, "Cosmetics, Household & Personal Care Industy Primer", Cosmetics, Household & Personal Care, pp. 1-191, (2017).
Breiden et al., "The Role of Sphingolipid Metabolism in Cutaneous Permeability Barrier Formation", Biochimica et Biophysica Acta, vol. 1841, pp. 441-452, (2014).
Cabasso et al., "*Drosophila melanogaster* Mutated in its GBA1b Ortholog Recapitulates Neuronopathic Gaucher Disease", J. Clin. Med, vol. 8, No. 1420, pp. 1-23, (2019).
Chauhan et al: "Pharmaceutical Screen Identifies Novel Target Processes for Activation of Autophagy with a Broad Translational Potential", Nature Communications, vol. 6, No. 1, pp. 1-15, (2015).
Chesselet and Anderson, "Final Report: Testing of Ambroxol in the Thy1-αSyn Mouse Model of PD", Presentation for the Michael J. Fox Foundation, date of publication on the internet: Feb. 6, 2017.
Choi et al., "Ambroxol Induces Autophagy and Potentiates Rifampin Antimycobacterial Activity", Antimicrobial Agents and Chemotherapy, vol. 62, Issue 9, pp. 1-5, (2018).
Choi et al., "Autophagy in Human Health and Disease", N Engl J Med, vol. 368, pp. 651-662, (2013).
Choi et al., "Enhanced Bioavailability of Ambroxol by Transdermal Administration of the EVA Matrix Containing Penetration Enhancer in Rats", Biomolecules & Therapeutics, vol. 18, No. 1, pp. 106-110 (2010).
Efeyan et al., "Nutrient Sensing Mechanisms and Pathways", Nature, vol. 517, pp. 302-310, (2015 ).
Farwick et al., "Developments in Cerarminde Identification, Synthesis, Function and Nomenclature", Cosmetics & Toiletries, vol. 124, No. 2, pp. 63-72, (2009).
Feingold et al., "Role of Lipids in the Formation and Maintenance of the Cutaneous Permeability Barrier", Biochimica et Biophysica Acta, vol. 1841, pp. 280-294, (2014).
Fluhr et al., "Transepidermal Water Loss Reflects Permeability Barrier Status: Validation in Human and Rodent In Vivo and Ex Vivo Models", Experimental Dermatology, vol. 15, pp. 483-492, (2006).
Galluzzi et al., "Pharmacological Modulation of Autophagy: Therapeutic Potential and Persisting Obstacles", Nature Reviews, vol. 16, pp. 487-511, (2017).
Granger et al., "Is Aging as Inevitable as Death and Taxes?", Cell Metabolism, vol. 23, pp. 947-948, (2016).

(Continued)

*Primary Examiner* — Rei Tsang Shiao
(74) *Attorney, Agent, or Firm* — Michele Wales; Inhouse Patent Counsel, LLC

(57) ABSTRACT

Compositions and methods for improving skin health and skin barrier function. Specifically, topical administration of compositions comprising low dose formulations of ambroxol can be used to improve skin barrier function.

23 Claims, 5 Drawing Sheets

(56) References Cited

OTHER PUBLICATIONS

Hall et al., "A Trial for the Ages", Science, vol. 349, Issue 6254, pp. 1274-1278, (2015).
Holleran et al., "Consequences of β-Glucocerebrosidase Deficiency in Epidermis", The Journal of Clinical Investigation, Inc., vol. 93, pp. 1756-1764, (1994).
International Preliminary Report of Patentability dated Aug. 6, 2020 and received in PCT/US19/15137.
International Search Report and Written Opinion dated Apr. 25, 2019 and received in PCT/US2019/015137.
International Search Report and Written Opinion dated Dec. 3, 2018 and received in PCT/US2018/042193.
International Search Report and Written Opinion dated Feb. 26, 2019 and received in PCT/US2019/015137.
Kern et al., "Ambroxol for the Treatment of Fibromyalgia: Science or Fiction?", Journal of Pain Research, vol. 10, pp. 1905-1929 (2017).
Kern K-U et al, "Topical Ambroxol for the Treatment of Neuropathic Pain", Schmerz, Der, Springer Verlag, Berlin, DE, vol. 29, No. 3, pp. S89-S96, (2015).
Lapierre et al., "Transcriptional and Epigenetic Regulation of Autophagy in Aging", Autophagy, vol. 11, No. 6, pp. 367-880, (2015).
Leslie et al., "A Putative Antiaging Drug Takes a Step From Mice to Men", Science, vol. 342, pp. 789, (2013).
Lim et al., "Aquatide Activation of SIRT1 Reduces Cellular Senescence Through a SIRT1-FOXO1-Autophagy Axis", Biomol Ther, vol. 25, No. 5, pp. 511-518, (2017).
Lopez et al., "The Hallmarks of Aging", Cell, vol. 153, pp. 1194-1217, (2013).
Magalhaes et al., "Effects of Ambroxol on the Autophagy-Lysosome Pathway and Mitochondria in Primary Cortical Neurons", Scientific Reports, vol. 8, No. 1385, pp. 1-12, (2018).
McNeill et al., "Ambroxol Improves Lysosomal Biochemistry in Glucocerebrosidase Mutation-Linked Parkinson Disease Cells", Brain, pp. 1-15, (2014).
Meckfessel et al., "The Structure, Function, and Importance of Ceramides in Skin and Their Use as Therapeutic Agents in Skin-Care Products", J Am Acad Dermatol, vol. 71, No. 1, pp. 177-184, (2014).
Migdalska-Richards et al., "Ambroxol Effects in Glucocerebrosidase and a-Synuclein Transgenic Mice", Ann Neural, pp. 766-775, (2016).
Monzon et al., "Ambroxol-Induced Systemic Contact Dermatitis Confirmed by Positive Patch Test", Research Letters, pp. 167-168, Document downloaded from http://www.elsevier.es, on Oct. 10, 2017.
Moors et al., "Therapeutic Potential of Autophagyenhancing Agents in Parkinson's Disease", Molecular Neurodegeneration, vol. 12, No. 11, pp. 1-18, (2017).
Nasto et al., "Biotech at the Beauty Counter", Nature Biotechnology, vol. 25, No. 6, pp. 617-619, (2007).
Notman et al., "The Permeability Enhancing Mechanism of DMSO in Ceramide Bilayers Simulated by Molecular Dynamics", Biophysical Journal, vol. 93, pp. 2056-2068, (2007).
Numan et al., "Ambroxol Hydrochloride, a Chaperone Therapy for Paget's Disease of Bone and Other Common Autophagy-Mediated Aging Diseases?", Integrative Clinical Medicine, vol. 1, No. 2, pp. 1-2, (2017).
Olshansky et al., "Measuring our Narrow Strip of Life ", Nature , vol. 538, pp. 175-176, (2016).
Orourke et al., "MXL-3 and HLH-30 Transcriptionally Link Lipolysis and Autophagy to Nutrient Availability", Nat Cell Biol., vol. 15, No. 6, pp. 668-676, (2013).
Partial Written Opinion and International Search Report dated Oct. 9, 2018 in PCT/US2018/042193.
Partridge et al., "Leading Edge Voices: Focus on Aging", Cell Metabolism, pp. 951-956, (2016).
Perera-Zoncu et al., "The Lysosome as a Regulatory Hub", Annu. Rev. Cell Dev. Biol., vol. 32, pp. 223-253, (2016).
Rinaldi et al., "Healing Beauty?", European Molecular Biology Organization, vol. 9, No. 11, pp. 1073-1077, (2008).
Shim et al., "A Protein Restriction-Dependent Sulfur Code for Longevity", Cell, vol. 160, pp. 15-17, (2015).
Tai et al., "Autophagy Impairment with Lysosomal and Mitochondrial Dysfunction is an Important Characteristic of Oxidative Stress-Induced Senescence", Autophagy, vol. 13, No. 1, pp. 99-113, (2016).
Van Smeden et al., "LC/MS Analysis of Stratum Corneum Lipids: Ceramide Profiling and Discovery", Journal of Lipid Research, vol. 52, pp. 1211-1221, (2011).
Van Smeden et al., "Combined LC/MS-Platform for Analysis of All Major Stratum Corneum Lipids, and the Profiling ol Skin Substitutes", Biochimica et Biophysica Acta, vol. 1841, pp. 70-79, (2014).
Wolf et al., "Barrier-Repair Prescription Moisturizers:Do We Really Need Them? Facts and Controversies", Clinics in Dermatology, vol. 31, pp. 787-791 (2013).
Ye et al., "Topical Applications of an Emollient Reduce Circulating Pro-Inflammatory Cytokine Levels in Chronically Aged Humans: a Pilot Clinical Study", European Academy of Dermatology and Venereology, pp. 1-7, (2019).
Office Action Received in Corresponding Japanese Application dated Jan. 13, 2023 (including English Translation).

* cited by examiner

Figure 4
Known sphingoid bases and fatty acids present in other ceramides indicate these 12 ceramide classes.

| Fatty acid / Sphingoid | Non-hydroxy fatty acid [N] | α-hydroxy fatty acid [A] | Esterified ω-hydroxy fatty acid [EO] |
|---|---|---|---|
| Dihydrosphingosine [DS] | CER[NDS] | CER[ADS] | CER[EODS] (not yet identified in SC) |
| Sphingosine [S] | CER[NS] | CER[AS] | CER[EOS] |
| Phytosphingosine [P] | CER[NP] | CER[AP] | CER[EOP] |
| 6-hydroxy sphingosine [H] | CER[NH] | CER[AH] | CER[EOH] |

USE OF AMBROXOL TO IMPROVE SKIN BARRIER FUNCTION

CROSS-REFERENCE TO RELATED APPLICATIONS

This application is a Continuation Application of U.S. Ser. No. 16/595,621, filed on Oct. 8, 2019, which is a Continuation Application of PCT/US19/15137 filed on Jan. 25, 2019, which claims priority to U.S. 62/622,375 filed on Jan. 26, 2018, all of which are hereby incorporated by reference in their entirety.

BACKGROUND OF THE INVENTION

Field of the Invention

The invention relates to the use of ambroxol to improve skin barrier function in a subject, preferably a human subject. Examples of such uses include increasing skin hydration, cosmetic uses, reduction of burns, scars, and/or rashes. The invention further relates to inhibiting and/or reducing transepidermal water loss (TEWL) and/or increasing the amount and/or concentration of ceramides (CER) in the skin's epidermis and/or hair by the topical application of ambroxol.

Discussion of the Related Art

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The major function of the skin is to form a barrier between the internal milieu of a host and environmental insults, such as chemicals, ultraviolet light, mechanical insults and pathogenic microorganisms. The skin's structure is made up of layers of cells and cellular-derived tissue, with the outermost set of layers being the epidermis. The surface layer is called the stratum corneum then, proceeding inwards: the stratum granulosum, stratum spinosum, stratum basale, and then the dermis layer. In addition, the palms of the hands and the soles of the feet have an additional layer, the stratum lucidum, between the stratum corneum and the stratum granulosum. Numerous products have been developed to improve the functioning and/or appearance of skin and hair.

For example, in 2016, the beauty and personal care market was close to a 500-billion-dollar industry. Repeated exposure to environmental insults, such as the sun, causes skin thinning, fragility and wrinkles. More serious sun exposure can cause a loss of skin elasticity, deep wrinkles, increased roughness and dryness, and altered pigmentation (age spots, skin spots). The skin can also become leathery, thickened in appearance which is characterized by deep furrows. Other environmental insults, such as chemicals causing burns and/or injury, acne or viral infection (e.g., chicken pox) can cause scaring, resulting in more serious and permanent damage to the skin.

Additionally, diseases can also cause changes in the skin's appearance. For example, Lupus patients often exhibit a characteristic rash, terms a "butterfly rash" that spans the face of the patient.

Additionally, the robustness and integrity of the skin, particularly with respect to its ability to respond to environmental stresses and/or resist disease, generally declines with age.

There are numerous different skin care formulations that are marketed as improving the appearance of the skin regardless of the type of skin insult. Examples of such formulations include, but are not limited to retinols, hydroxyl acids, Coenzyme Q10, copper peptides, Kinetin, and/or tea extracts. Even though numerous creams, oils, topicals and oral products are launched every month, there is an ongoing need for new regimens that are safe and effective in improving the functioning of a subject's largest organ—the skin.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The invention relates to ambroxol compositions and use thereof to improve skin barrier function. Specifically, the invention relates to improving skin barrier function of a subject, preferably a human, comprising administering to the subject an effective amount of ambroxol. Ambroxol can be administered as a composition with other components for topical delivery to a subject's skin and/or hair. In preferred embodiments, a topical composition comprising a low dose formulation of ambroxol is used to improve skin barrier function. In further preferred embodiments, skin barrier function is improved by up to about 10%, 20%, 30%, 40%, 50%, 60%, or 70% as compared to untreated control subjects.

A skin's barrier function can be improved with topical administration of ambroxol as measured by:
a. quickening the recovery of the skin barrier function after an insult;
b. decreasing the delay in the skin barrier recovery, as often occurs in premature infants or the elderly;
c. decreasing/preventing transepidermal water loss (TEWL);
d. decreasing/preventing electrolyte loss in the skin;
e. decreasing/preventing dry skin;
f. decreasing/preventing pruritus;
g. decreasing/healing/preventing skin lesions;
h. increasing/improving skin hydration;
i. improving protection from foreign insults (e.g., antimicrobial barrier);
j. increasing ceramide (CER) and/or glucosyl-ceramide production, preferably in the stratum basale, stratum spinosum, stratum granulosum, and/or stratum corneum layers of the skin;
k. increasing conversion of glucosyl-CERs into CER, preferably in the stratum granulosum and stratum corneum layers of the skin;
l. increasing the amount and/or concentration of CER in the skin, preferably in the stratum corneum layer of the skin;

m. increasing glucocerebrosidase activity in the stratum basale, stratum spinosum, stratum granulosum, and/or stratum corneum layers of the skin; or n. decreasing the overall rate of loss of robustness of the skin upon aging, according to generally accepted functional metrics that monitor such a decline, wherein the percentage change (i.e., increase or decrease) of (a)-(n) is at least 10%, 15%, 20%, 25%, 30%, 35%, 40%, 45%, 50%, 55%, 60%, or 65% as compared to the untreated state.

In a further preferred embodiment, topical formulations of ambroxol as described herein can be used to improve overall appearance of the skin, including treating, reversing and/or preventing symptoms of skin aging or damage, such as wrinkles, fine lines, discoloration, loss of tone, loss of elasticity, thinning and the like, by activating autophagy within skin cells.

Compositions of ambroxol formulations are provided in a variety of forms suitable for topical application, such as cosmetics, lotions, creams, shampoos, serums, sprays, skin lotions, and cleansers. Similarly, ambroxol formulations are provided in a kit comprising a cleanser, a spray essence, a lotion, a serum and an anti-aging night cream.

Additionally, ambroxol formulations can be used to help remove toxins at the cellular level, as well as helping boost skin's integrity to:

a. prevent cellular damage;
b. repair cellular damage;
c. rebuild and repair the skin's structural network;
d. reinvigorate skin cell function; and/or
e. repair, remove and/or recycle damaged cellular components for healthier functioning cells.

In further preferred embodiments, topical formulations of ambroxol as described herein can be used to induce autophagy within the skin cells.

In preferred embodiments, the concentration of CER that is increased in the stratum corneum after topical administration of ambroxol is at least 10%, 20%, 30%, 40%, 50% or 60% higher as when compared to the concentrations of cholesterol or free fatty acids or other suitable benchmarks.

By improving the skin barrier function, the appearance of the skin and/or hair is also improved. Such improvements include but are not limited to reducing the signs of aging (or premature aging), such as for example, decreasing the aging process of the skin, reducing the appearance of lines (e.g., fine lines) and/or wrinkles, decreasing skin sagging and/or imperfections, and/or improving and/or promoting skin elasticity or suppleness, and/or increasing and/or promoting retention of fluid in the skin. In other embodiments, the appearance of the skin and/or hair includes but is not limited to, reducing sun damage (particularly UV radiation-induced oxidative stress/photodamage), stretch marks, and/or scars, reducing the appearance of burns, reducing the appearance of blemishes (e.g. acne), reducing the appearance of dark circles, age spots, and other hyperpigmentation, reducing skin thickness, loss of elasticity and/or collagen content, reducing dry skin and/or puffiness, preventing water loss of the skin, and/or increasing moisturization, and/or reducing lentigines, freckles, and/or melasmas. Topical administration also includes the application of ambroxol to hair.

Many medications, cosmetics and inflammatory skin diseases, in addition to adverse reactions to chemical peels, ingredients, pesticides, chemicals, detergents, heat, laser resurfacing, laser assisted hair removal and skin injuries, can also be a source of pigmentation disorders. These pigmentation disorders can also be treated by ambroxol as described herein.

Other uses of topical administration of ambroxol as described herein include, but are not limited to, treatment of: atopic dermatitis, psoriasis; patients using topical tretinoin, premature infants, burns, and the elderly.

In some embodiments, enantiomers, analogs, esters, amides, prodrugs, or metabolites of ambroxol, including salts thereof and particularly a pharmaceutically acceptable salt can be used. In preferred embodiments, the salt of ambroxol is a hydrochloride.

In preferred embodiments, the topical administration of ambroxol occurs at a low dose formulation. As used herein a "low dose formulation" comprises a concentration of ambroxol of less than 0.1% (w/w), and more preferably, less than 0.01% (w/w), and even more preferably between 0.01%-0.09% (w/w), and even more preferably between 0.001%-0.01% (w/w), and even more preferably between 0.0001-0.001% (w/w), and even more preferably between 0.00001-0.0001% (w/w). In further preferred embodiments, the low dose formulation concentration of ambroxol for topical administration occurs at about 0.00001% (w/w), 0.00002% (w/w), 0.00003% (w/w), 0.00004% (w/w), 0.00005% (w/w), 0.00006% (w/w), 0.00007% (w/w), 0.00008% (w/w), 0.00009% (w/w), 0.0001% (w/w), 0.0002% (w/w), 0.0003% (w/w), 0.0004% (w/w), 0.0005% (w/w), 0.0006% (w/w), 0.0007% (w/w), 0.0008% (w/w), 0.0009% (w/w), 0.001% (w/w), 0.002% (w/w), 0.003% (w/w), 0.004% (w/w), 0.005% (w/w), 0.006% (w/w), 0.007% (w/w), 0.008% (w/w), 0.009% (w/w), 0.01% (w/w), 0.02% (w/w), 0.03% (w/w), 0.04% (w/w), 0.05% (w/w), 0.06% (w/w), 0.07% (w/w), 0.08% (w/w), or 0.09% (w/w), as well as any combination of these low dose formulation concentrations. It is unexpected and not suggested in the literature that ambroxol could improve skin barrier function at such low formulation concentrations.

Ambroxol can be formulated with other compounds for topical administration as described herein. For example, ambroxol formulations can include ceramides. Preferred examples of such ceramides include but are not limited to: Ceramide 1 (EOS), Ceramide 2 (NS), Ceramide 3 (NP), Ceramide 4 (EOH), Ceramide 5 (AS), Ceramide 6 (NH), Ceramide 7 (AP), Ceramide 8 (AH), or Ceramide 9 (EOP).

In further embodiments, the invention includes a long-term use of ambroxol for improving skin barrier function, the method comprising topically administering a therapeutically effective amount of ambroxol, wherein the administration of the compound is at least for 1, 2, 3, 4, 5, 6, 7, 8, 9, or 10 years. Administration of ambroxol could be topically applied several times over a given period of time, e.g., once daily, twice daily dose, three times daily.

In further preferred embodiments, the appearance of the skin (due to, for example, dryness, scarring, hyperpigmentation, etc) is improved, or promoted, by up to 10%, 20%, 30%, 40%, 50%, 60%, or 70% as compared to untreated control subjects.

In preferred embodiments, the subject is a mammal, and even in further preferred embodiments, the mammal is a human.

BRIEF DESCRIPTION OF THE DRAWINGS

FIG. 4 shows the 12 ceramide classes based on known sphingoid bases and fatty adds.

DETAILED DESCRIPTION

I. Definitions

Figure 1:
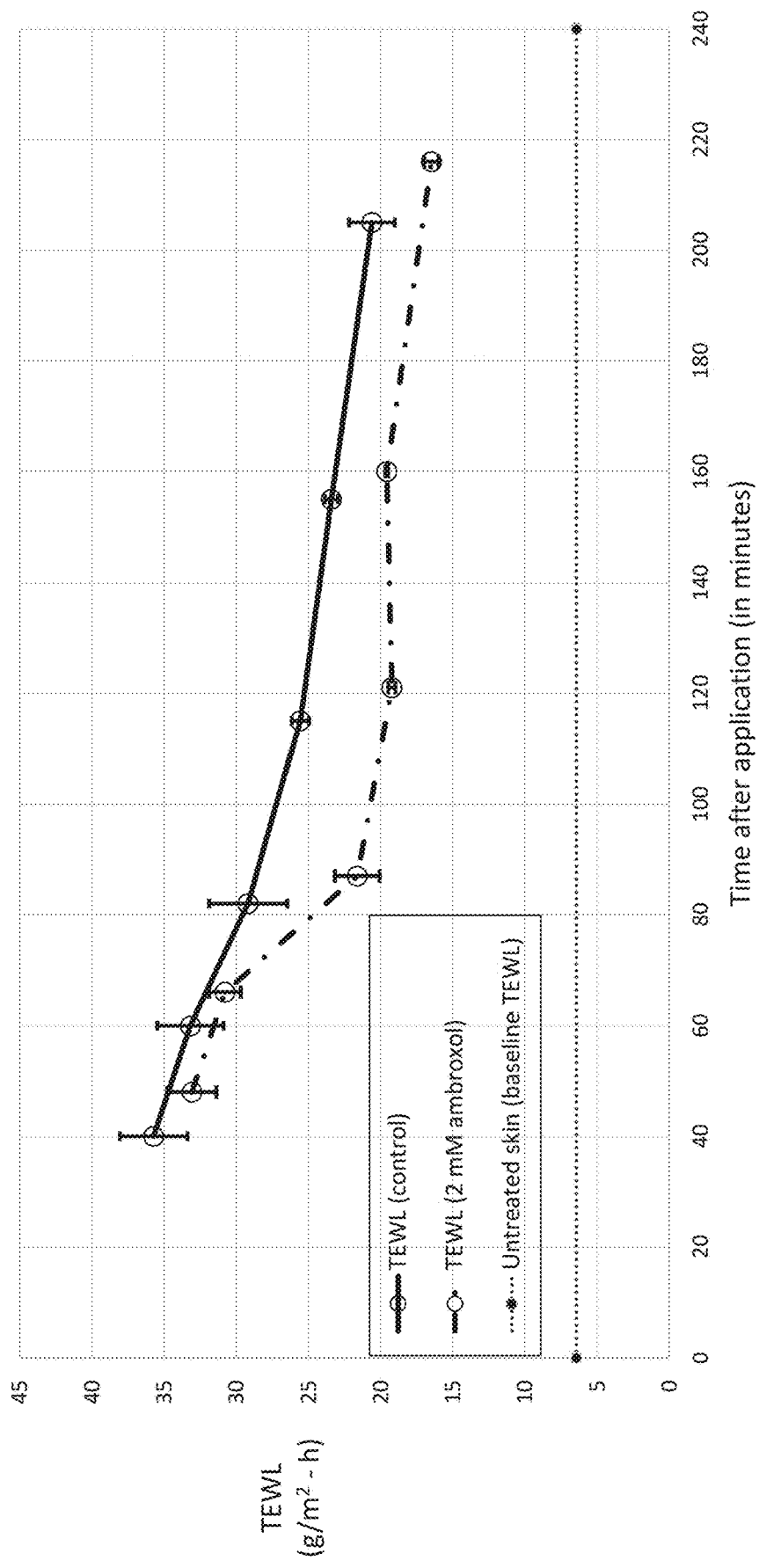
FIG. 1 shows the results of the time course of the return of TEWL towards the baseline value with ambroxol in 100% dimethyl sulfoxide.

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

The present invention can "comprise" (open ended) or "consist essentially of" the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention.

As used herein, a "subject" is a vertebrate, preferably a mammal, more preferably a human. Mammals include, but are not limited to, murines, simians, humans, farm animals, sport animals, and pets. In other preferred embodiments, the "subject" is a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), or an ape (e.g., gorilla, chimpanzee, orangutan, gibbon). In other embodiments, non-human mammals, especially mammals that are conventionally used as models for demonstrating therapeutic efficacy in humans (e.g., murine, primate, porcine, canine, or rabbit animals) may be employed. In preferred embodiments, an "individual" or "patient" (as in the subject of the treatment) means mammals, particularly non-human primates, e.g. apes and monkeys, and most particularly humans.

As understood herein, an "effective amount" of a topical composition of the instant invention refers to an amount of the composition suitable to elicit a beneficial response in the subject, e.g., for improving skin barrier function, such as for example, increasing skin hydration, CER production, and/or healthy aging of the skin and/or to decrease TEWL in a subject.

The term "dose" or "dosage" as used herein refers to physically discrete units suitable for administration to a subject, each dosage containing a predetermined quantity of the active pharmaceutical ingredient calculated to produce a desired response.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2 fold, of a value. Unless otherwise stated, the term 'about' means within an acceptable error range for the particular value, such as ±1-20%, preferably ±1-10% and more preferably ±1-5%. In even further embodiments, "about" should be understood to mean +/−5%.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All percentages and ratios used herein are by weight of the total composition unless otherwise indicated herein. All temperatures are in degrees Celsius unless specified otherwise. All measurements made are at an ambient air temperature of 18-25° C., at normal atmospheric pressure, and at a relative humidity of 30-50%, unless otherwise designated.

All ranges recited herein include the endpoints, including those that recite a range "between" two values. Terms such as "about," "generally," "substantially," "approximately" and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

Where used herein, the term "and/or" when used in a list of two or more items means that any one of the listed characteristics can be present, or any combination of two or more of the listed characteristics can be present. For example, if a composition of the instant invention is described as containing characteristics A, B, and/or C, the composition can contain A feature alone; B alone; C alone; A and B in combination; A and C in combination; B and C in combination; or A, B, and C in combination.

The term "isolated compound" means a compound substantially free of contaminants or cell components with which the compound naturally occurs, or the reagents used in synthesis or the byproducts of synthesis. "Isolated" and "substantially free of contaminants" does not mean that the preparation is technically pure (homogeneous), but it is sufficiently pure to provide the compound in a form in which it can be used therapeutically.

As used herein, "skin barrier function" or a "skin's barrier function" is used consistently with its usage in the art—mainly to describe the function of the skin (which includes hair) to protect a subject from external hazards, including microbial, chemical and/or mechanical insults. As used herein, the skin barrier function can be measured by numerous ways, including: (a) the amount of time needed to recover the skin barrier function after an insult; (b) the amount of transepidermal water loss (TEWL); (c) the amount of electrolyte loss; (d) the amount and/or healing time of dry skin; (e) the amount and/or healing time of pruritus; (f) the amount and/or healing time of skin lesions; (g) the amount of skin hydration; (h) the ability to protect a subject from foreign insults (e.g., antimicrobial barrier); (i) the amount and/or efficiency of ceramide (CER) and/or glucosyl-CER production, preferably in the stratum basale, stratum pinosum, stratum granulosum, and/or stratum corneum layers of the skin; (j) the amount and/or efficiency in converting glucosyl-CERs into CER, preferably in the stratum granulosum and stratum corneum layers of the skin; (k) the amount and/or concentration of CER in the skin, preferably in the stratum corneum layer of the skin; and/or (l) glucocerebrosidase (GCE) activity in the stratum basale, stratum spinosum, stratum granulosum, and/or stratum corneum. Methods for measuring skin barrier function are well known and well described in the literature. See, for example, Antonov et al., "Methods for the Assessment of Barrier Function," Curr Probl Dermatol. Basel, Karger, 2016, vol 49, pp 61-70; Feingold and Elias "Role of Lipids in the Formation and Maintenance of the Cutaneous Permeability Barrier" Biochimica et Biophysica Acta 1841:280-294 (2014); Breiden and Sandhoff, "The Role of Sphingolipid Metabolism in Cutaneous Permeability Barrier Formation," Biochimica et Biophysica Acta 1841:441-452 (2014) as well as the references cited therein, all of which are incorporated by reference in their entirety.

Besides the biochemical measures used to evaluate "improved skin barrier function", topical administration of ambroxol as described herein can be measured visually, such as, for example, by improved cosmetic signs of aging or the means of reducing the risk of occurrence, delaying the onset, slowing the progression, and/or reducing the severity and/or manifestation, of a sign of aging and/or degeneration of the skin, and including, but not limited to, preventing the occurrence, development or progression of a sign of aging and/or degeneration of the skin. Other preferred embodiments include, decreasing the aging process of the skin, reducing the appearance of lines (e.g., fine lines) and/or wrinkles, decreasing skin sagging and/or imperfections, and/or improving and/or promoting skin elasticity or suppleness, and/or increasing and/or promoting retention of fluid in the skin. In other embodiments, an improved skin barrier function can be demonstrated by reducing sun damage (particularly UV radiation-induced oxidative stress/photodamage), stretch marks, and/or scars, reducing the appearance of burns, reducing the appearance of blemishes (e.g. acne), reducing the appearance of dark circles, age spots, and other hyperpigmentation, reducing skin thickness, loss of elasticity and/or collagen content, reducing dry skin and/or puffiness, preventing water loss of the skin, and/or increasing moisturization, and/or reducing lentigines, freckles, and/or melasmas.

As used herein, "autophagy" describes the fundamental process for degrading and recycling cellular components. During autophagy, damaged, unnecessary, dysfunctional macromolecules and organelles are broken down and are recycled for building new cellular components. In particular, autophagy makes it possible to regulate, repair and eliminate proteins with a long service life in the cells, thus promoting cellular homeostasis during differentiation and aging of human skin. Autophagy is thought to play a role in skin care. Moreover, ambroxol has been shown to modulate autophagy. See, for example PCT/US2018/042193 (herein incorporated by reference in its entirety.)

As used herein, "ceramide" refers to a molecule composed of a sphingoid base conjugated to a fatty acid via an amide bond and includes the 12 different subclasses (shown in FIG. 4); at least 11 of these 12 subclasses are known to be associated with human skin. Ceramides are prominent lipids found in stratum corneum, the outermost layer of epidermis, and have an important function in the formation and retention of the skin barrier in the stratum corneum. Pseudoceramides have similar structures to natural ceramides. Skin damage caused by detergents which remove the lipids essential for the barrier function will result in an increased transdermal water loss (TEWL), and deteriorated barrier function has negative consequences for the total condition of the skin. A damaged skin barrier leads to increased skin sensitivity and potential irritation such as atopic dermatitis or psoriasis. Topical applications of ceramide or pseudoceramide containing compositions are effective in relieving atopic eczema. Ceramide or pseudoceramide also exhibit therapeutic properties such as wound and ulcer healing through the promotion of cell restoration and growth.

Figure 5:
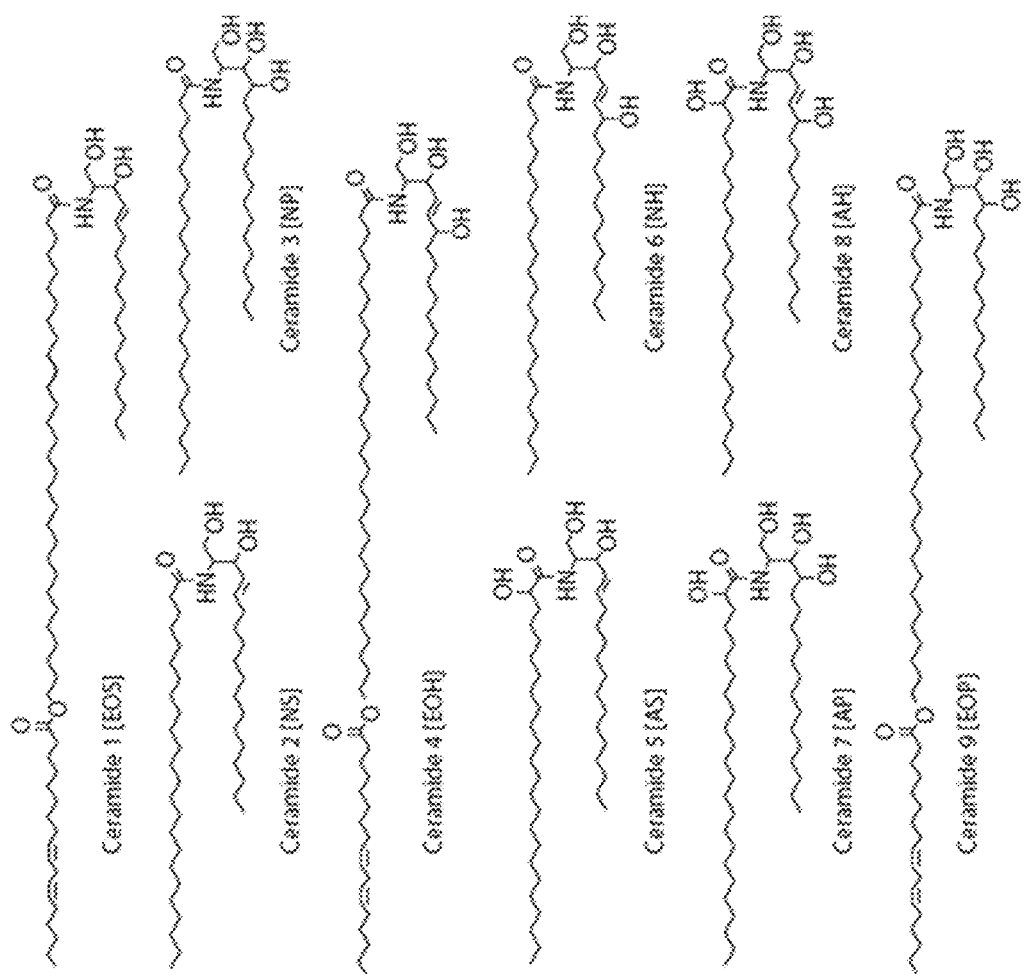
FIG. 5 shows the chemical structures and nomenclature for some ceramides. Chemical structure and nomenclature of CER of the SC; A=α-Hydroxy fatty acid, EO=Ester-linked ω-Hydroxy acid, N=Nonhydroxy fatty acid, P=Phytosphingosine, S=Sphingosine and H=6-Hydroxysphingosine; Ceramide X=Nacyl dihydrosphingosine co-migrates with ceramide 2 and is not included in this general analysis.

Over 340 different species of ceramides have been classified based on the composition of the head group or esterification of the fatty acid. Currently there are four different sphingoid bases and 3 different types of fatty acids. FIG. 5 outlines the chemical structures and nomenclature of the different classes of ceramides. See, also, Farwick et al. "Developments in Ceramide Identification, Synthesis, Function and Nomenclature," Cosmetics & Toiletries, Vol 124, No. 2 (2009). As used herein, preferred ceramides used in combination with ambroxol, include, but are not limited to ceramides selected from: Ceramide EOS, Ceramide NS, Ceramide NP, Ceramide EOH, Ceramide AS, Ceramide NH, Ceramide AP, Ceramide AH, Ceramide EOP, Ceramide NdS, Ceramide AdS, and/or Ceramide EOdS.

As used herein, the phrase, "cosmetically acceptable delivery vehicle" is used to describe the components of the formulation other than the active ingredients of the ambroxol formulation that are generally recognized as safe and nontoxic at the levels employed to achieve 100% weight of the formulation applied or delivered to the skin surface. A cosmetically acceptable vehicle may take the form of any known in the art that is suitable for application to skin. The vehicle may comprise an aqueous phase, an oil phase, an alcohol, a silicone phase or mixtures thereof. The cosmetically acceptable vehicle may also comprise an emulsion. Non-limiting examples of suitable cosmetically acceptable vehicles are disclosed in U.S. Pat. No. 9,238,000, entitled, "Method of Improving Aging Appearance of Skin by Modulation of WIPI-1"; the teachings are incorporated herein by reference.

As used herein, a "cleanser" is formulated with ambroxol as described herein to gently exfoliate dead skin cells, dissolve pore-clogging impurities, soothe and condition and prepare skin for the rest of regimen. Examples of additional components that can be included in a cleanser formulation include but are not limited to pomegranate extract to gently remove excess oil and dulling impurities to re-texturize skin and tighten appearance of pores and Tsubaki oil and rosehip oil to reduce inflammation and replenish essential lipids for improved texture and a comfortable after feel.

As used herein, an "essence" product is formulated with ambroxol as described herein to protect the skin from harmful environmental stressors, rehydrate, soothe and condition the skin. Additional components that can be added to an essence include but are not limited to green tea extract to achieve a pH-balancing mist that shields the skin from environmental pollutants and aggressors while sealing in hydration and soothing skin and/or orange peel oil to help detoxify skin, while high potency antioxidants including polyphenols, white tea, vitamin B and vitamin C offer all day protection from free radicals. In addition, nourishing fruit extracts and hyaluronic acid can be added to the delivery vehicle to revive dehydrated and dull skin, reduce puffiness and discourage the formation of wrinkles.

As used herein, a "serum product" formulated with ambroxol as described herein promotes, inter alia, cellular regeneration, improves firmness and elasticity, reduces discolorations, brightens complexion, enhances skin tone and texture. Additional components of a serum formulation can include an oil/water emulsion to achieve a serum that gives back to the skin what it naturally loses over time and the ability to self-repair; probiotics and Vitamin D3 to encourage skin renewal and support collagen and elastin production, enhancing firmness and elasticity: licorice root, niacinamide and Vitamin C can be included in the delivery vehicle to reduce dark spots and brighten skin tone for a noticeably glowing complexion. The lightweight formula and ingredients adapt to the skin's unique needs and reignite luminosity, elasticity and suppleness.

As used herein a "day cream" can be formulated with ambroxol to also include a UVA and UVB broad spectrum SPF 30 ingredient, reduce redness and inflammation, prevent collagen breakdown from damaging free radicals, provide all-day hydration and plump the skin. Other components that can be added, include but are not limited to an oil/water emulsion to achieve a day cream that delivers a precise balance of hydration and protection to actively combat the visible signs of aging. SPF 30 defends against harmful ultraviolet (UV) rays and free radicals while fighting wrinkles and visibly plumping skin, such as for example, UVA and UVB broad spectrum SPF 30 ingredients, and/or antioxidants to protect from the sun's damaging rays and neutralize free radicals, peptides and plant stem cells to improve collagen production to visibly lift sagging skin and prevent the onset of wrinkles. Hyaluronic acid and tremella mushroom can also be added to the delivery vehicle to deeply hydrate for smooth, plump skin.

As used herein, a "night cream" is formulated with ambroxol to deeply moisturize and balance natural oils, lift, firm and sculpt facial contours, reduce depth of fine lines and wrinkles and revitalize dull, tired skin. Other components that can be added to a night cream formulation include but are not limited to a light oil/water emulsion to achieve a night cream that provides the skin with unique support needed to maximize repair and renewal during sleep. Such components include but are not limited to argan oil, Vitamin B5 and hyaluronic acid to hydrate, nourish and combat dry, dull skin and improve barrier function. Peptides along with Vitamins A and C can be included in the delivery vehicle to encourage collagen and elastin production improving firmness and diminishing the appearance of fine lines and wrinkles for smooth, plump skin. The rich, whipped texture deeply nourishes skin and redefines facial contours overnight to produce a firm and glowing complexion when waking.

As used herein, a "booster" product is formulated with ambroxol to help effectively up-regulate the skin autophagy and/or skin barrier function for dramatically younger-acting skin, which can reduce, for example, visible lines while increasing skin elasticity. The delivery vehicle in booster formulations can include Vitamin C, Vitamin D, Vitamin B3 and omega-6 oil to target and treat visible lines while increasing skin elasticity.

Compounds of the Invention

Ambroxol, also known by its chemical name trans-4-(2-amino-3,5-dibromobenzylamino) cyclohexanol, has the structure as shown in Table 1. As used herein, reference to "ambroxol" throughout the specification includes all salts of ambroxol. One example of such a salt is the a hydrochloride salt also shown in Table 1.

TABLE 1

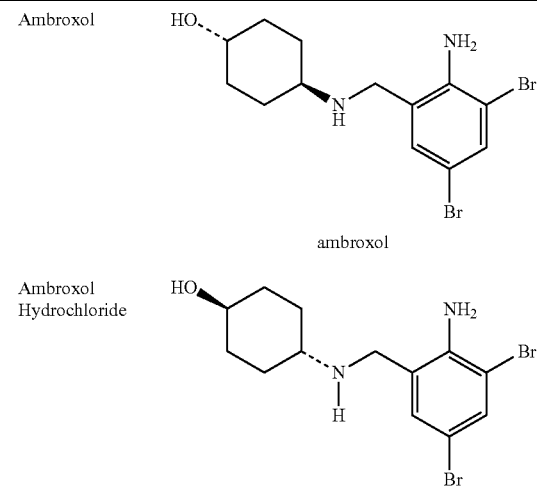

The term "salts" embraces addition salts of free acids or free bases. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of therapeutic compounds.

Suitable pharmaceutically-acceptable acid addition salts may be prepared from an inorganic acid or from an organic acid. Examples of inorganic acids include, but are not limited to, hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and salfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, s-hydroxybutyric, salicylic, galactaric, oxalic, malonic and galacturonic acid. Examples of pharmaceutically unacceptable acid addition salts include, for example, perchlorates and tetrafluoroborates. All of these acid addition salts maybe prepared from ambroxol by reacting, for example, the appropriate acid with the compound.

Suitable pharmaceutically acceptable base addition salts of ambroxol include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, m eglumine (N-methyl glucamine) and procaine. Examples of pharmaceutically unacceptable base addition salts include lithium salts and cyanate salts. All of these base addition salts may be prepared from ambroxol by reacting, for example, the appropriate base with the compound.

Ambroxol, including its salts, are known and may be prepared by methods known to the person skilled in the art of organic synthesis. For example, U.S. Patent Application publication number US2004/0242700, incorporated herein by reference in its entirety, provides a synthetic protocol for the preparation of ambroxol.

Topical Compositions

In an aspect, the invention includes a composition comprising a therapeutically effective amount of ambroxol, in conjunction with a pharmaceutically acceptable excipient for topical administration to improve skin barrier function. Ambroxol may be administered in the form of a topical composition, in combination with a pharmaceutically acceptable carrier.

Ambroxol has been used topically in patients for the treatment of pain. See, Kern and Weiser, "Topical Ambroxol for the Treatment of Neuropathic Pain," Der Schmerz, Suppl 3, 29: S89-96 (2015). Here, a topical formulation comprising 20% ambroxol was tested on patients to determine whether ambroxol would alleviate and/or eliminate pain. The authors reported that the pain reduction at this concentration was between 33 and 100% which they deemed clinically relevant. Importantly, the authors reported that no skin changes were observed even though other case reports suggested ambroxol caused systemic contact dermatitis. See, Monzon et al., "Ambroxol-Induced Systemic Contact Dermatitis Confirmed by Positive Patch Test," Allergol Immunolpathol 37:167-169. Thus, it was known in the literature before the filing of this invention that ambroxol either caused adverse skin changes or had no effect on the skin's appearance.

However, it is surprisingly unexpected that doses substantially less than 20% would in fact improve skin conditions. It is believed that topical administration of ambroxol to improve skin barrier function can occur at formulation concentrations of less than 0.1% (w/w), and more preferably, less than 0.01% (w/w), and even more preferably between 0.001%-0.01% (w/w), and even more preferably between 0.0001-0.001% (w/w), and even more preferably between 0.00001-0.0001% (w/w). Ranges of formulation concentrations, all less than 0.1% (w/w) as described herein are also specifically contemplated. It is unexpected and not suggested in the literature that ambroxol could improve skin barrier function at such low formulation concentrations.

"Pharmaceutically acceptable carrier" means any carrier, diluent or excipient which is compatible with the other ingredients of the formulation and not deleterious to the recipient. The active agent may be formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. For examples of the preparation of ambroxol is disclosed in, for example, Examples 1-8 of WO2005/007146, or its equivalent US2005/00148747, incorporated herein by reference.

For topical administration, ambroxol may be mixed with a suitable carrier or diluent such as water, an aqueous buffer, an oil (particularly a vegetable oil), ethanol, saline solution, aqueous dextrose (glucose) and related sugar solutions, glycerol, or a glycol such as propylene glycol or polyethylene glycol. Solutions for topical administration preferably contain a water-soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for topical administration may take the form of an aqueous or non-aqueous solution, dispersion, suspension or emulsion.

In preferred embodiments, ambroxol is formulated with a solvent that enables ambroxol to permeate the upper layers of the skin. In preferred embodiments, the solvent is an organic solvent, such as for example, dimethyl sulfoxide.

Suitable permeation promoters according to the invention are urea, dimethyl sulfoxide (DMSO), hyaluronic acid sodium salt, alkanols such as laurylalcohol or oleylalcohol, alkanoic acids such as oleic acid, 1-dodecylazacycloheptan-2-one, ethyleneglycol, propyleneglycol or menthol, as well as other permeation promoters selected from among the 1-acylglycosides, 1-acyl-polyoxyethylenes, 1-acyl-saccharides, 2-n-acyl-cyclohexanones, 2-n-acyl-1,3-dioxolanes (SEPA), 1,2,3-triacyl-glycerols, 1-alkanols, 1-alkanoic acids, 1-alkyl-acetates, 1-alkyl-amines, 1-alkyl-n-alkyl-polyoxyethylenes, 1-alkyl-alkylates, n-alkyl-beta-D-thioglycosides, 1-alkyl-glycerides, 1-alkyl-propyleneglycols, 1-alkyl-polyoxyethylenes, 1-alkyl-2-pyrrolidones, alkyl-acetoacetates, alkyleneglycols, alkylmethylsulphoxides, alkyl-propionates, alkylsulphates, diacylsuccinates, diacyl-N,N-dimethylaminoacetates (DDAA), diacyl-N,N-dimethylaminoisopropionates (DDAIP) and phenylalkylamines.

Topical formulations may also be combined with at least one excipient such as fillers, binders, humectants, disintegrating agents, solution retarders, absorption accelerators, wetting agents, absorbents or lubricating agents.

Topical compositions comprising low dose formulations of ambroxol may further comprise ceramides, which are well known in the art. See, for example, Meckfessel and Brandt, "The Structure Function and Importance of Ceramides in Skin and Their Use as Therapeutic Agents in Skin-Care Products," J Am Acad Dermatol 2014; 71:177-84 (herein incorporated by reference in its entirety.) In further preferred embodiments, the topical formulation is used several times, giving doses over a period of time, e.g., a daily dose or twice daily treatment for a week or more.

Examples of ceramides that can be formulated with ambroxol as described herein include, but are not limited to: Ceramide EOS, Ceramide NS, Ceramide NP, Ceramide EOH, Ceramide AS, Ceramide NH, Ceramide AP, Ceramide AH, Ceramide EOP, Ceramide NdS, Ceramide AdS, and/or Ceramide EOdS.

In further embodiments, the invention includes a long-term method of use in a subject, and/or to treat, inhibit, and/or reduce the skin aging process, skin age-related symptoms, and/or the skin age-related diseases, and/or to improve skin barrier function, preferably in a human, the method comprising administering a therapeutically effective amount of ambroxol, wherein the administration of the compound is at least for 1, 2, 3, 4, 5, 6, 7, 8, 9, or 10 years.

In further preferred embodiments, skin barrier function is improved by up to about 10%, 20%, 30%, 40%, 50%, 60%, or 70% as compared to untreated control subjects. In further preferred embodiments, the skin barrier function is improved by at least 10%, 20%, 30%, 40%, 50%, 60%, or 70% as compared to untreated control subjects. Ways to measure skin barrier function are well known in the art and described herein.

The topical compositions of the present invention may also be formulated so as to provide slow or controlled release of ambroxol therein using, for example, hydropropylmethylcellulose in varying proportions to provide the desired release profile, other polymer matrices, gels, permeable membranes, osmotic systems, multilayer coatings, microparticles, liposomes and/or microspheres. In these embodiments, these formulations are ideally suited for improving skin barrier function.

In general, a controlled-release preparation is a topical composition capable of releasing ambroxol at the required rate to maintain constant pharmacological activity for a desirable period of time. Such dosage forms provide a supply of a drug to the body during a predetermined period of time and thus maintain ambroxol levels in the therapeutic range for longer periods of time than conventional non-controlled formulations.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the ambroxol in the topical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is placed on the skin having a body temperature high enough to induce gel formation of the sol-gel matrix, thereby releasing ambroxol.

Without further description, it is believed that one of ordinary skill in the art can, using the preceding description and the following illustrative examples, make and utilize the compounds of the present invention and practice the claimed methods. The following examples, therefore, specifically point out the preferred embodiments of the present invention, and are not to be construed as limiting in any way the remainder of the disclosure. Although the invention herein has been described with reference to embodiments, it is to be understood that these embodiments, and examples provided herein, are merely illustrative of the principles and applications of the present invention. It is therefore to be understood that numerous modifications can be made to the illustrative embodiments and examples, and that other arrangements can be devised without departing from the spirit and scope of the present invention as defined by the appended claims. All patent applications, patents, literature and references cited herein are hereby incorporated by reference in their entirety.

EXAMPLES

Example 1. Restoration of Skin Barrier Function after Disruption by Dimethyl Sulfoxide Dimethyl sulfoxide (DMSO) is a well-known skin permeability enhancer that is thought to act by disrupting ceramide-containing lipid bilayers of the stratum corneum and thereby compromising the permeability barrier of the skin (Agner and Serup, Clin. Expt. Dermatology 14:214 [1989]; Notman et al Biophysical Journal 93:2056 [2007]). Among its many protective functions, this lipid barrier regulates transepidermal water loss (TEWL) and is vital for the prevention of skin dryness in mammals. Thus, it is accepted by researchers in the field, that measurements of TEWL can be used to directly assay the integrity of the skin permeability barrier (Fluhr et al Experimental Dermatology 15:483 [2006]).

To test ambroxol's ability to improve TEWL (i.e., reduce the rate of water loss), Ambroxol-HCl (MW 414.6, EP grade, Shilpa Medicare Ltd., Raichur, Karnataka—584 102, India) was dissolved to a concentration of 2.0 mM (0.075% solution [w/w]) in 99.9% pure dimethyl sulfoxide (EP grade, Heiltropfen, Germany). 20 microliter aliquots of the 2.0 mM ambroxol solution in DMSO as well as the 99.9% pure DMSO were spread onto patches of human (adult male) skin in the upper thigh area; the area of skin covered by the solutions in each case was approximately 2 cm$^2$. All experiments were conducted in a narrow range of relative humidity (30-40%) and at stable room temperatures of 18-22° C.

Transepidermal water loss (TEWL) measurements, in units of g/m$^2$·h, were taken at various time points after applying the solutions (at t=0) to the skin sites. TEWL values were assessed using a wireless closed-chamber system (VapoMeter, Delphin Technologies Ltd., Kuopio, Finland) that automatically calculates water evaporation rates over a small area (~1.3 cm$^2$); each measurement took about 10 s (Fluhr et al Experimental Dermatology 15:483 [2006]). Prior to the beginning of the experiment, and at the conclusion of the experiment, TEWL measurements of adjacent untreated skin areas were recorded; the baseline TEWL of untreated skin was found to not change significantly during the course of the experiment. All time points were measured in duplicate or triplicate. FIG. 1 shows the results of this experiment. Both the "control" (DMSO only) curve and the "2 mM ambroxol" (DMSO containing 2.0 mM ambroxol) curve initially show a slow trend back towards the baseline (pre-treatment) TEWL, reflecting the natural post-disruption reestablishment of the skin barrier (Agner and Serup, Clin. Expt. Dermatology 14:214 [1989]). However, at about 60 minutes post-application, the ambroxol curve exhibited a sudden drop in TEWL, indicating a rapid burst of skin barrier healing over a period of approximately 30 minutes. The improvement in TEWL, a difference of 4-6 g/m$^2$·h between the two curves, then maintains itself over the remaining course of the experiment. This indicates that the burst of improvement in the transepidermal water loss between 60-90 minutes post-application led to a durable improvement in the skin barrier. [Symbols: Solid line, DMSO (control with no ambroxol); dot-dashed line, 2.0 mM ambroxol in DMSO; dotted line, untreated skin from areas adjacent to the treatment sites. Shown for each point are the error bars (standard deviation of duplicate or triplicate measurements); for some points the error bars are less visible because they were smaller than the diameter of the symbol representing that point.]

Example 2. Restoration of Skin Barrier Function after Disruption by a Dimethyl Sulfoxide-Containing Aqueous Formulation An alternative skin disruption agent, involving an aqueous formulation, was tested to see whether this might affect the skin barrier restoration properties of ambroxol. Accordingly, a 2.0 mM solution of ambroxol was prepared using 60% DMSO (60:40 DMSO:water [v/v]) mixture as the solvent. 60% DMSO has been reported to be the minimum concentration of DMSO needed to disrupt ceramide-containing lipid bilayers in skin (Notman et al Biophysical Journal 93:2056 [2007]).

Figure 2:
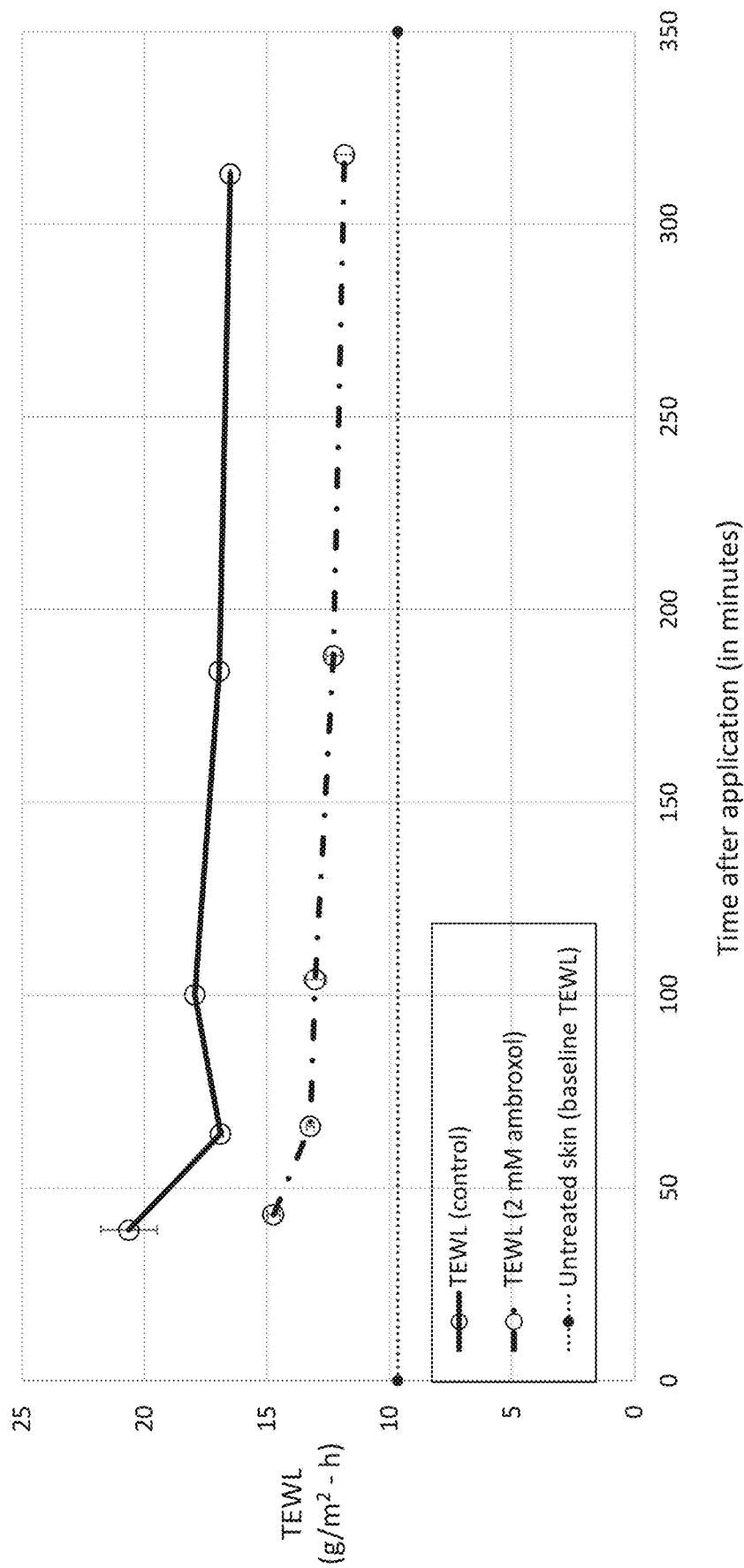
FIG. 2 shows the results of the time course of the return of TEWL towards the baseline value with ambroxol in an alternative formulation of 60% dimethyl sulfoxide: 40% water [v/v].

Experimental conditions were essentially identical to those used in Example 1, except 10 microliter aliquots of the 2.0 mM ambroxol solution in DMSO:water (60:40 [v/v]), or the DMSO:water solution alone as a control, were spread onto patches of human skin in the upper thigh area. Results are shown in FIG. 2. All time points were measured in duplicate or triplicate.

Like the experiment shown in FIG. 1, both the control and the ambroxol-treated skin exhibit a slow approach to the baseline TEWL level over a period of hours. Also like in the experiment shown in FIG. 1, there is an enduring improvement of approximately 5 g/m$^2$-h in the rate of water loss of the ambroxol-treated skin relative to skin treated with the DMSO:water formulation alone. However, in this case the burst occurs earlier in the time course, in the first hour post-application (for practical reasons the earliest time point in this series was about 40 minutes post-application, and the burst had already started at that point). This indicates that by altering the ambroxol formulation the kinetics of skin barrier improvement can be modulated. [Symbols: Solid line, 60:40 (v/v) DMSO:water (control with no ambroxol); dot-dashed line, 2.0 mM ambroxol in 60:40 (v/v) DMSO:water; dotted line, untreated skin from areas adjacent to the treatment sites. Shown for each point are the error bars (standard deviation of duplicate or triplicate measurements); for some points the error bars are less visible because they were smaller than the diameter of the symbol representing that point.]

Example 3. Effect of Ambroxol Dosage on TEWL

Figure 3:
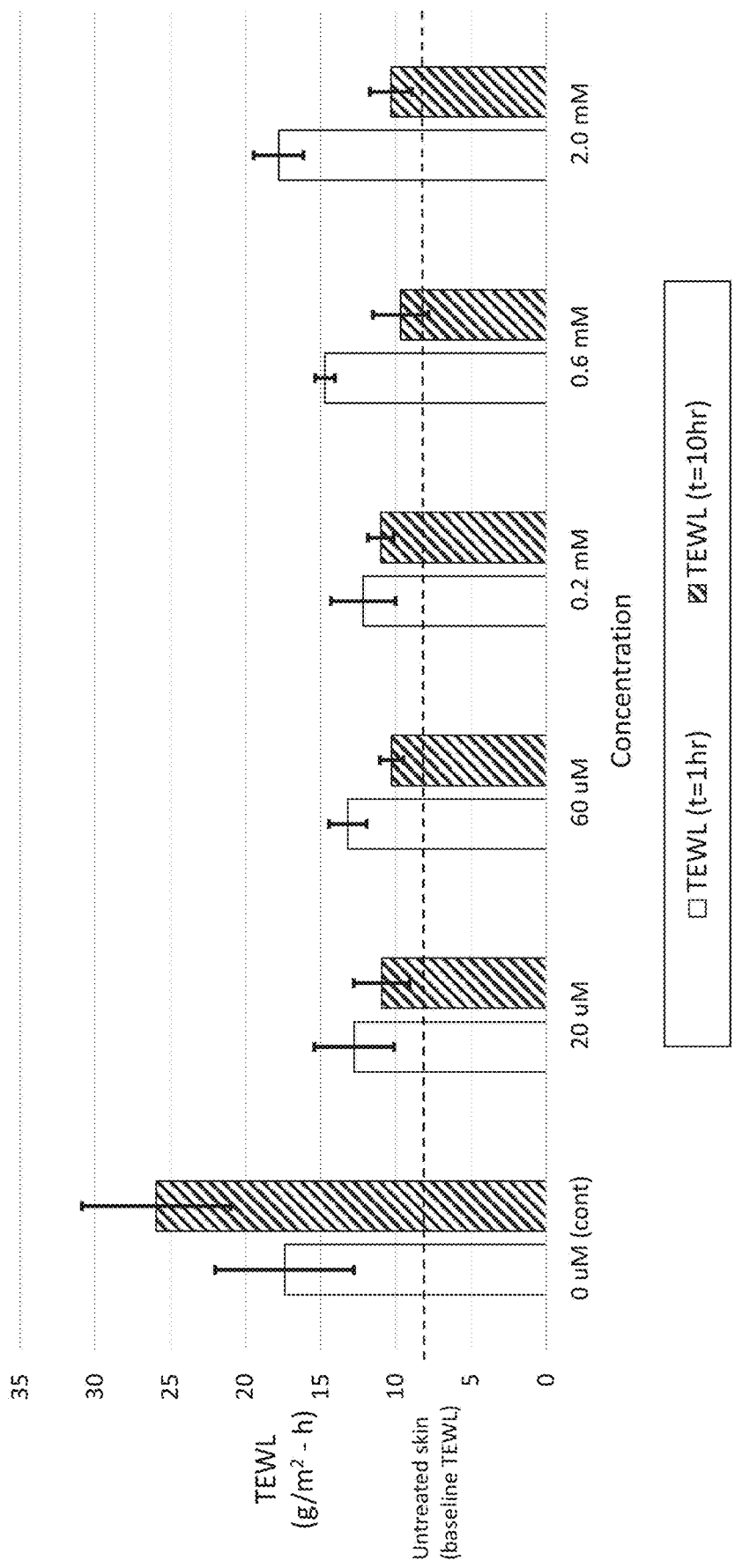
FIG. 3 shows the effect of various ambroxol concentrations on TEWL, where the ambroxol concentration ranges from 20 uM to 2.0 mM.

FIG. 3 shows a dose-ranging study testing ambroxol concentrations of 20 micromolar, 60 micromolar, 0.2 mM, 0.6 mM, and 2.0 mM. Apart from these additional concentrations, conditions and the formulation (99.9% DMSO) were essentially the same as those described in Example 1, except in this experiment 10 microliter aliquots were spread and the skin region tested was on the volar forearm.

The data in FIG. 3 are presented as histograms, with only start points (at 1 hr post-application) and end-points (at 10 hr post application) shown. Two things are notable about this experiment. One, in contrast to the other experiments, the control skin treated with DMSO alone did not regress to the baseline during the 10 hour time-window of data collection, as was observed with the experiments in Examples 1 and 2; in fact, the TEWL seemed to get slightly worse during that time period. This may reflect the relative delicacy of volar forearm skin compared to skin of the upper thigh, such that the same treatment may be more or less harsh depending on the skin area treated. The second notable result from this experiment was that even concentrations of ambroxol much lower than 2.0 mM yielded positive results in terms of ameliorating the increase in TEWL caused by the DMSO insult to the skin barrier. In fact, sub-millimolar concentrations of ambroxol may even be optimal for skin care in some contexts. [Symbols: Open rectangles, skin TEWL measured at 1 hr post-application; hatched rectangles, skin TEWL measured at 10 hr post-application; dashed line, average TEWL value (7.8±1.1 g/m$^2$-hr) of untreated skin from areas adjacent to the treatment sites. All measurements were made in quadruplicate (n=4) or quintuplicate (n=5). Shown for each value are the error bars (standard deviation of quadruplicate or quintuplicate measurements.]

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a subject suffering from psoriasis or atopic dermatitis in a subject, wherein said method comprises topically administering a composition comprising a low dose formulation of ambroxol, wherein said low dose formulation comprises less than 0.1% (w/w) of ambroxol.

2. The method of claim 1, wherein the method improves skin barrier function, wherein said skin barrier function is measured by:
   1) a reduction in the signs of aging (or premature aging),
   2) a decrease in the aging process of the skin,
   3) a reduction in the appearance of lines and/or wrinkles,
   4) a decrease in skin sagging,
   5) an improvement and/or promotion in skin elasticity or suppleness,
   6) a reduction in sun damage,
   7) a reduction in stretch marks,
   8) a reduction in the appearance of scars,
   9) a reduction in the appearance of burns,
   10) a reduction in the appearance of blemishes (e.g. acne),
   11) a reduction in the appearance of dark circles,
   12) a reduction in the appearance of age spots,
   13) a reduction in the appearance of puffiness,
   14) a prevention in water loss of the skin, and/or
   15) an increase in moisturization.

3. The method according to claim 2, wherein the skin barrier function is improved by up to about 10%, 20%, 30%, 40%, 50%, 60%, or 70% as compared to untreated control subjects.

4. The method of claim 2, wherein the skin barrier function is improved by:
   a. a quickening of the recovery of the skin barrier function after an insult;
   b. a decrease in the delay in the skin barrier recovery;
   c. a decrease or prevention in transepidermal water loss (TEWL);
   d. a decrease or prevention of electrolyte loss in the skin;
   e. a decrease or prevention of dry skin;
   f. a decrease or prevention of pruritus;
   g. a decrease or prevention of skin lesions;
   h. an increase or improvement in skin hydration;
   i. an improvement in protection from foreign insults (e.g., antimicrobial barrier);
   j. an increase in ceramide (CER) and/or glucosyl-ceramide production, preferably in the stratum basale, stratum spinosum, stratum granulosum, and/or stratum corneum layers of the skin;
   k. an increase in conversion of glucosyl-CERs into CER, preferably in the stratum granulosum and stratum corneum layers of the skin;
   l. an increase in the amount and/or concentration of CER in the skin, preferably in the stratum corneum layer of the skin;
   m. an increase in glucocerebrosidase activity in the stratum basale, stratum spinosum, stratum granulosum, and/or stratum corneum; and/or n. a decrease in the overall rate of loss of robustness of the skin upon aging, according to generally accepted functional metrics that monitor such a decline;

wherein an increase or decrease of any one of (a)-(n) at least 10%, 15%, 20%, 25%, 30%, 35%, 40%, 45%, 50%, 55%, 60%, or 65% as compared to the untreated state.

5. The method of claim 4, wherein the concentration of CER that increased in the stratum corneum is at least 10%, 20%, 30%, 40%, 50% or 60% higher as when compared to the concentrations of cholesterol and/or free fatty acids or other suitable benchmarks.

6. The method of claim 2, wherein the improved skin barrier function is measured by increasing and/or improving skin appearance, skin elasticity, healthy skin aging and/or skin moisture in a subject.

7. The method of claim 2, wherein the improved skin barrier function is measured by inhibiting, and/or reducing skin aging, a skin age-related symptom, and/or a skin age-related disease in the subject.

8. The method of claim 1, wherein the method decreases/prevents transepidermal water loss (TEWL).

9. The method of claim 1, wherein composition comprises ambroxol hydrocholoride.

10. The method of claim 9, wherein the composition further comprises a ceramide.

11. The method of claim 10, wherein the ceramide is selected from: Ceramide EOS, Ceramide NS, Ceramide NP, Ceramide EOH, Ceramide AS, Ceramide NH, Ceramide AP, Ceramide AH, Ceramide EOP, Ceramide NdS, Ceramide AdS, and/or Ceramide EOdS.

12. The method of claim 1, wherein autophagy within the skin cells is also induced.

13. The method of claim 1, wherein composition is topically applied several times over a given period of time, e.g., once daily, twice daily dose, three times daily.

14. The method of claim 1, wherein the composition is topically applied for at least 1, 2, 3, 4, 5, 6, 7, 8, 9, or 10 years.

15. The method of claim 1, wherein the low dose formulation concentration of ambroxol is:
(a) less than 0.01% (w/w);
(b) between 0.01%-0.09% (w/w);
(c) between 0.001%-0.01% (w/w);
(d) between 0.0001-0.001% (w/w);
(e) between 0.00001-0.0001% (w/w);
(f) at about 0.00001% (w/w), 0.00002% (w/w), 0.00003% (w/w), 0.00004% (w/w), 0.00005% (w/w), 0.00006% (w/w), 0.00007% (w/w), 0.00008% (w/w), 0.00009% (w/w), 0.0001% (w/w), 0.0002% (w/w), 0.0003% (w/w), 0.0004% (w/w), 0.0005% (w/w), 0.0006% (w/w), 0.0007% (w/w), 0.0008% (w/w), 0.0009% (w/w), 0.001% (w/w), 0.002% (w/w), 0.003% (w/w), 0.004% (w/w), 0.005% (w/w), 0.006% (w/w), 0.007% (w/w), 0.008% (w/w), 0.009% (w/w), 0.01% (w/w), 0.02% (w/w), 0.03% (w/w), 0.04% (w/w), 0.05% (w/w), 0.06% (w/w), 0.07% (w/w), 0.08% (w/w), or 0.09% (w/w).

16. The method of claim 15, wherein said low dose formulation comprises less than 0.01% (w/w) of ambroxol.

17. The method of claim 16, wherein autophagy is induced in the skin cell.

18. The method of claim 17, wherein the concentration of CER is increased in the stratum corneum by at least 10%, 20%, 30%, 40%, 50% or 60% higher than it was prior to treatment, relative to the concentrations of cholesterol and/or free fatty acids and/or other suitable benchmarks, such as the concentrations of reference molecules in the stratum corneum that are known to be unaffected by the treatment.

19. The method of claim 18, wherein the composition comprises ambroxol hydrochloride.

20. The method of claim 19, wherein the composition further comprises a ceramide.

21. The method of claim 20, wherein the ceramide is selected from: Ceramide EOS, Ceramide NS, Ceramide NP, Ceramide EOH, Ceramide AS, Ceramide NH, Ceramide AP, Ceramide AH, Ceramide 9 (EOP), Ceramide NdS, Ceramide AdS, and/or Ceramide EOdS.

22. The method of claim 1, wherein the composition is formulated as a lotion, spray, cream, shampoo, serum, emulsion, gel, oil, mask, essence, toner or paste.

23. The method of claim 1, wherein the composition further comprises essential fatty acid, preferably omega-3 or omega-6 oil.

* * * * *